(12) United States Patent
Haupt et al.

(10) Patent No.: US 7,694,567 B2
(45) Date of Patent: Apr. 13, 2010

(54) ACOUSTIC DETECTION OF HIDDEN OBJECTS AND MATERIAL DISCONTINUITIES

(75) Inventors: Robert Haupt, Lexington, MA (US); Ken Rolt, Westford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 636 days.

(21) Appl. No.: 11/400,544

(22) Filed: Apr. 7, 2006

(65) Prior Publication Data

US 2006/0225509 A1 Oct. 12, 2006

Related U.S. Application Data

(60) Provisional application No. 60/670,004, filed on Apr. 11, 2005.

(51) Int. Cl.
G01N 9/24 (2006.01)
(52) U.S. Cl. .............................. 73/627; 73/594; 73/604; 73/657
(58) Field of Classification Search .................. 73/627, 73/598, 599, 600, 602, 604, 606, 653, 654, 73/657, 594; 367/88, 99; 381/77, 79
See application file for complete search history.

(56) References Cited

U.S. PATENT DOCUMENTS 3,812,454 A * 5/1974 Bhuta et al. ..................... 367/7

| | | | |
|---|---|---|---|
| 4,823,908 A * | 4/1989 | Tanaka et al. ................ 181/175 |
| 4,922,467 A * | 5/1990 | Caulfield ....................... 367/87 |
| 5,357,063 A * | 10/1994 | House et al. ................. 181/108 |
| 5,563,848 A | 10/1996 | Rogers et al. |
| 5,672,825 A * | 9/1997 | Uno et al. ...................... 73/579 |
| 6,081,481 A | 6/2000 | Sabatier et al. |
| 6,144,176 A * | 11/2000 | Quinlan ....................... 318/460 |
| 6,229,899 B1 * | 5/2001 | Norris et al. ................... 381/77 |
| 6,545,945 B2 * | 4/2003 | Caulfield ....................... 367/87 |
| 6,678,381 B1 * | 1/2004 | Manabe ......................... 381/77 |
| 6,823,737 B2 * | 11/2004 | Kepler et al. .................. 73/602 |
| 6,862,252 B1 * | 3/2005 | Hickling ........................ 367/88 |
| 6,899,027 B2 * | 5/2005 | Kersch ....................... 101/228 |
| 6,973,830 B2 * | 12/2005 | Pepper et al. ................. 73/602 |
| 7,113,447 B1 | 9/2006 | Matthews et al. |
| 7,162,042 B2 * | 1/2007 | Spencer et al. ................ 381/77 |
| 7,210,785 B2 * | 5/2007 | Matsuzawa .................. 353/15 |
| 7,453,223 B2 * | 11/2008 | Buck et al. ................... 318/432 |
| 7,456,599 B2 * | 11/2008 | Piefer et al. ................. 318/625 |
| 2005/0248233 A1 | 11/2005 | Pompei |
| 2006/0109989 A1 * | 5/2006 | Linhard ....................... 381/160 |

FOREIGN PATENT DOCUMENTS

EP 0973152 1/2000

* cited by examiner

*Primary Examiner*—J M Saint Surin
(74) *Attorney, Agent, or Firm*—Goodwin Procter LLP

(57) ABSTRACT

Sonic excitation is used to locate, without contact, an object or defect beneath a surface. Defects may include, for example, damage and flaws in load bearing concrete structures wrapped in plastic, fiberglass or composite sheathing, while buried objects amenable to detection include landmines or above-ground mines.

12 Claims, 2 Drawing Sheets

ACOUSTIC DETECTION OF HIDDEN OBJECTS AND MATERIAL DISCONTINUITIES

RELATED APPLICATION

This application claims the benefits of and priority to U.S. Provisional Application Ser. No. 60/670,004 (filed on Apr. 11, 2005), the entire disclosure of which is hereby incorporated by reference.

GOVERNMENT SUPPORT

This invention was made with government support under Grant Number F19628-00-C-0002, awarded by the U.S. Air Force. The government has certain rights in the invention.

BACKGROUND

Acoustic energy is used in numerous applications to characterize discontinuities within various types of material. Acoustically based techniques rely on differences in mechanical properties between a feature of interest and its surroundings. These differences result in different vibrational responses to sonic excitation, which may be detected and the feature thereby localized and/or characterized.

An important advantage of acoustic techniques is the ability to detect discontinuities corresponding to (or indicating the presence of) flaws or hidden items that may not be detectable using visual or other techniques. Such discontinuities may represent latent defects that can compromise the mechanical integrity of load-bearing structures, dangerous concealed objects, or even buried landmines. A related advantage of acoustic detection is the standoff distance it affords. The ability to avoid physical contact may be desirable for reasons of convenience or safety.

SUMMARY OF THE INVENTION

In preferred embodiments, the present invention utilizes a parametric acoustic array (PAA) that emits a highly directional acoustic or sound beam. Desirably, this acoustic beam is initially emitted at frequencies above audible sound, but the acoustic beam actually reaching the target has a much lower frequency in the audible range. Desirably, the PAA utilizes high-frequency (e.g., ultrasonic) transducers set in an array, which enables the production of the acoustic beam. The high-frequency output of the transducers is modulated with a low-frequency signal. The nonlinearity of the air demodulates the signal so that the low-frequency component reaches the target of interest. The sound beam generated by the parametric array can be designed to minimize the sound pressure level outside of the beam to a level that will not cause human discomfort or harm.

A high-powered PAA in accordance with the invention may, for example, generate and transmit a highly directional acoustic beam that can exceed sound pressure levels of 100 dB to ranges beyond 10 meters at audible frequencies greater than 1000 Hz. This source may be used to insonify targets from distances exceeding 10 meters. The vibration field of the target can then be measured with a laser vibrometer or other suitable vibration-detection device to locate or identify a feature of interest without physical contact. One application of the present invention is to locate, without contact, damage and flaws in load-bearing concrete structures wrapped in plastic, fiberglass or composite sheathing from close range or standoff ranges exceeding 10 meters. Another application is to locate buried objects such as landmines, or above-ground mines that produce a sonically detectable signature.

In contrast to the present invention, current prototype acoustic landmine-detection systems typically operate within 1-7 meters of the landmine target, and generally employ a conventional loudspeaker. Exceeding a standoff range of 7 meters is a difficult challenge. While an array of speakers could achieve the acoustic power requirements, the massive size and weight of the array would be impractical for many forms of operational use. Moreover, the sound level close to an array of speakers would be well above the hearing threshold of pain, thus reducing safety and comfort for the operator and others nearby. This is exacerbated by the omni-directional nature of loudspeaker sound sources, a problem solved by the present invention.

The standoff-beam acoustic source of the invention can be used with a laser vibrometer or other vibration-measurement system and can aid or be used as an alternative to invasive and contact measurement techniques. The equipment is portable and can evaluate more surface area of a target at a faster rate than currently practiced contact and invasive measurement techniques.

Accordingly, in a first aspect, the invention comprises a method of localizing an object or defect beneath a surface. In accordance with this approach, a directive ultrasonic acoustic beam including a modulated, inaudible high-frequency signal and an audible low-frequency signal is generated. The acoustic beam is directed through the air at the surface and the air causes demodulation of the acoustic beam and entry of the low-frequency signal into the surface. Vibrations at the surface characteristic of the object or defect are detected to thereby localize the object or defect.

In some embodiments, the acoustic beam is generated by an acoustic source less than 10 meters from the target, whereas in other embodiments, the acoustic source is more than 10 meters from the target. The object or defect may, for example, be a landmine located beneath the ground. Alternatively, the object or defect may be a void beneath a sheath enveloping a concrete structure.

In a second aspect, the invention comprises a method of detecting damage in a concrete structure having a sheath thereover. The method comprises sonicating the structure to excite vibrations in the sheath, and measuring the vibrations to detect anomalies therein characteristic of damage in the concrete structure. In some embodiments, the structure is sonicated using a parametric acoustic array. In other embodiments, the structure is sonicated using at least one loudspeaker.

In a third aspect, the invention comprises a system for localizing an object or defect beneath a surface. The system includes an acoustic source for generating a directive ultrasonic acoustic beam including a modulated, inaudible high-frequency signal and an audible low-frequency signal; a vibration detector for detecting, without physical contact, vibrations at the surface caused by the acoustic beam; and an analysis module for localizing the object or defect based on the detected vibrations.

In some embodiments, the acoustic source comprises a parametric acoustic array. In other embodiments, the acoustic source comprises at least one loudspeaker. The detector may be a laser vibrometer.

BRIEF DESCRIPTION OF THE DRAWINGS

The foregoing discussion will be understood more readily from the following detailed description of the invention when taken in conjunction with the accompanying drawings.

DETAILED DESCRIPTION

Figure 1A:
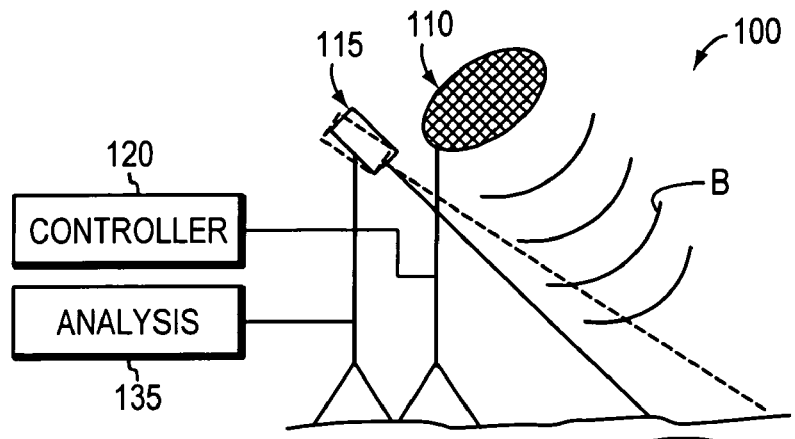
FIG. 1A schematically illustrates a system in accordance with the invention.

Refer first to FIG. 1A, which illustrates an exemplary detection system 100 in accordance with the invention. The system includes a PAA 110 and a laser vibrometer 115. A controller 120 governs the operation of PAA 110, directing the beam B that it produces and scanning it over an area of interest—the ground in FIG. 1A, in which an object 130 (e.g., a landmine) is buried. In general, the buried object can be any acoustically reflecting, nonporous object or discontinuity buried a few centimeters to a few meters below a porous surface. The object 130 creates a discontinuity in the acoustical impedance of the soil that can be detected by remote sensing. By "soil" or "ground" is herein meant any porous earth regardless of composition.

Controller 120 may include programming that causes PAA 110 to scan an area automatically or according to a pre-programmed (e.g., sweep) pattern. Alternatively or in addition, controller 120 may include a user-operated device such as a joystick that facilitates direct user control of the beam scan. Controller 120 may interface with PAA 110 through a wireless or wired connection.

An analysis module 135 includes circuitry and programming for reading the output of laser vibrometer 115 and correlating the output with the physical location being scanned. Analysis module 135 typically receives vibrometer output as an analog signal (either wirelessly or via a wired connection), and may analyze the signal in this form for signatures characteristic of the feature of interest (e.g., a landmine). Alternatively, however, analysis module 135 (or laser vibrometer 115) may include analog-to-digital conversion circuitry and a memory for storing the vibrometer output in digital form, where it may be subjected to computational analysis. Observed signals may be compared to stored signatures elicited by features or objects of interest, thereby facilitating identification of the items responsible for an observed signal. Comparison may be made based on, for example, a threshold degree of pattern matching, an amplitude threshold, averaged signal characteristics, heuristic rules, or similar metrics. Alternatively, the signal may be analyzed in accordance with the parameters and relationships discussed below.

Analysis module 135 may, if desired, store substantial quantities of output for later analysis, and may include programming for performing this analysis and a display for depicting the results. Stored vibrometer readings may be associated with data indicative of the location being scanned, so that, for example, the reading associated with a specific location (or area) of interest can be reviewed at a later time.

More generally, analysis module 135 may be implemented on a personal computer (e.g., a PC with an INTEL processor), or on a wireless device, telephone, personal digital assistant, information appliance, workstation, or other suitable computing device with adequate computational and memory capacity. Functionality such as analog-to-digital conversion, as well as analysis of raw signal data as discussed below, may be realized in hardware or software, or a combination of both. Programming may be written in any suitable high-level computer language, such as FORTRAN, PASCAL, C, C++, C#, Java, Tcl, or BASIC, or in an assembly language. Furthermore, the program can be written in a script, macro, or functionality embedded in commercially available software, such as EXCEL or VISUAL BASIC. The programming may be embedded on an article of manufacture including, but not limited to, "computer-readable program means" such as a floppy disk, a hard disk, an optical disk, a magnetic tape, a PROM, an EPROM, or CD-ROM.

Parametric Acoustic Array

Parametric acoustic arrays derive their name from their similarity to the parametric amplifier, which combines two RF signals, a pump and an input, together with nonlinear mixing to form a modulation product. The modulation product is an RF wave that is translated (up or down) in frequency from the pump frequency. The pump signal provides the input energy for the amplifier and is modulated in amplitude by the input signal. The PAA combines pump acoustical signals, typically ultrasonic, at two different frequencies, $\omega_1$ and $\omega_2$, to form a modulation envelope. The modulation envelope undergoes natural mixing to generate new frequency components in the modulation product because of the nonlinear behavior of the fluid; this process is called self-demodulation. The useful part of the modulation product for the PAA is always the difference frequency $\omega_d$, where $\omega_d=|\omega_1-\omega_2|$; the signal amplitude at this difference frequency grows progressively with propagation. Full or partial amplitude modulation of a singletone pump acoustic wave can also produce a modulation product.

PAA 110 is preferably an end-fire-steered, continuously distributed volume of difference-frequency sources created during the self-demodulation process. This volume is confined within the main-radiation-axis near field of the pump. The near-field difference-frequency sources are cumulative in strength. They have amplitudes that grow progressively with range from the pump source, and can be thought of as being coherently stimulated in a traveling-wave end-fire sense by the pump carrier. Hence the PAA borrows the terminology, and in some sense the physics, of the parametric amplifier in RF practice, end-fire arrays from antenna theory, and the pump and coherent stimulation found in lasers.

A suitable PAA is described in U.S. Patent Application Publication 2005/0248233 and European Patent No. 0973152, the entire disclosures of which are hereby incorporated by reference. As disclosed therein, carrier frequencies of at least 60 kHz so that the modulation products have frequencies well above the human audible range and are therefore likely harmless to individuals who are within the ultrasonic fields of the system 100. The ultrasonic signals may be generated by an array of membrane transducers (e.g., electrostatic transducers), which couple to the atmosphere more efficiently than piezoelectric transducers. The transducers may be driven with circuits in which the capacitances of the transducers resonate with circuit inductances at the acousto-mechanical resonant frequencies of the transducers. This provides a very efficient transfer of electrical energy to the transducers, thereby facilitating the use of relatively high carrier frequencies.

In general, a plurality of transducers are incorporated into a transducer module and the modules are arranged and/or electrically driven so as to provide, in effect, a large radiating surface and a large non-linear interaction region. With this arrangement, the system can generate a relatively high sound level without an unduly high beam intensity, as might be the case with the use of a transducer arrangement having a smaller radiating surface and interaction region, which is driven to generate a higher ultrasonic intensity to accomplish the same level of audible energy transmission. Controller 120 can mechanically or electronically scan the beam to direct its center to different locations by delaying the transmission of selected elements in the PAA transducer array. The beam width can also be modified with element delays to widen or tighten the beam diameter. Alternatively, the transmitted beam can be steered by physically rotating the array or using a rotatable reflecting plate, or by altering the phase relationships of the individual transducer modules in the array.

Thus, a suitable parametric sound system includes a transducer array comprising a plurality of ultrasonic transducer modules arranged in a two- or three-dimensional configuration. Each of the modules preferably contains a plurality of transducers, which are driven by a signal generator by way of a phasing network. The network applies variable relative phases to the signals applied to the transducers in order to facilitate electronic focusing, steering, or otherwise modifying the distribution of ultrasound radiated by the array. Alternatively, because the signal is wideband, it is possible to use delay—i.e., a constant relative phase shift across all frequencies—rather than variable phase shifting to steer the beam.

In preferred embodiments, PAA 110 generates audible difference-frequency sound in an end-fire volumetric array. This end-fire array results from the coherent stimulation of the difference-frequency wave as it propagates and builds in amplitude. Thus the volume of air in front of the PAA can be thought of as a virtual loudspeaker. The pump modulation envelope is generated in a narrow beam within the near field of the transducer array. As the modulation envelope propagates, a nonlinear interaction occurs with air, causing acoustic self-demodulation. An audible difference frequency is produced but the narrow beam shape of the pump is maintained. Within the near field, the nonlinear reaction builds to a range where the difference-frequency sound pressure achieves a maximum. When the modulation envelope reaches the end of the near field of the transducer array, it attenuates rapidly as a result of geometric spreading, and the nonlinear self-demodulation effectively ends. The audible difference frequency, however, generated in the near field and generated as an end-fire array, continues to propagate as a linear acoustic wave. Eventually, the audible difference frequency also loses power from the effects of attenuation and geometrical spreading with distance.

The self-demodulation process of PAA 110 is inefficient because only a small percentage of the initial pump energy is converted to the difference-frequency wave. Typically, this loss can be on the order of 20 to 80 dB. Although a loss of this magnitude is quite large, PAA 110 can convert a narrow ultrasonic beam into an extremely directive lower-frequency sound. This conversion would otherwise require an enormous array of loudspeakers. PAA 110 can generate a difference-frequency wave that maintains the narrowness of the high-frequency pump beam at a considerable range.

Optimization of the end-fire array length can be accomplished by choosing a pump frequency, PAA cross-sectional area, and input electrical power to produce minimal characteristic lengths that are approximately the same for two or three competing effects. For example, the longest end-fire array length occurs for the 15-kHz pump frequency where the aperture and attenuation lengths coincide at the same range at 15 meters. In turn, the difference-frequency pressure amplitude increases to its maximum at 15 meters, where it then falls off because of the effects of spherical spreading and attenuation.

Our preferred PAA emphasizes operational constraints. A 15-kHz pump frequency is in the audible frequency band and would have a sound-pressure level that approaches 160 to 170 dB, which would be dangerous to people without heavy-duty hearing protection. In contrast, a pump frequency in the ultrasonic band would have minimal effects to the operator and others in the vicinity of the equipment and object to be detected. Choosing a pump frequency just above the audible band, such as 24 kHz, would result in a decrease in the end-fire array length, compared to the 15-kHz pump frequency. However, the net loss in the difference-frequency pressure power would be only 5 dB and would still provide ample power to excite an object at a reasonable standoff range. We have found that the largest power is observed at a range between five and 10 meters, which corresponds to the end-fire array length of a 24-kHz pump frequency. The output difference-frequency power falls from high frequency to low frequency and is proportional to the square of the difference frequency. These results indicate that PAA 110 can produce acceptable difference-frequency power levels above the detection threshold at frequencies approximately 500 Hz and higher, and at ranges up to 30 meters from the transducer array.

Laser Vibrometer

Suitable laser vibrometers include a laser that emits a beam of radiant energy that is divided, by a refractive beam splitter, into a reference beam and a target beam. An acousto-optic modulation unit (e.g., a Bragg cell) displaces the frequency of the laser light by adding or subtracting a carrier frequency component corresponding in magnitude to the anticipated frequency of the seismic oscillations of the ground. A beam of radiant energy from the modulation unit reflects off the ground. Backscattered laser light is reflected by a scanning mirror to a photodetector, where it combines with the reference beam to produce an interference pattern. Changes in the ground caused by the sonic energy radiated by PAA 110 change the interference pattern and, consequently, the output of the photodetector. Analysis module 135 eliminates the carrier frequency from the output of the photodetector so that only the modulation carrier frequency and the seismic vibrations are present.

Figure 1B:
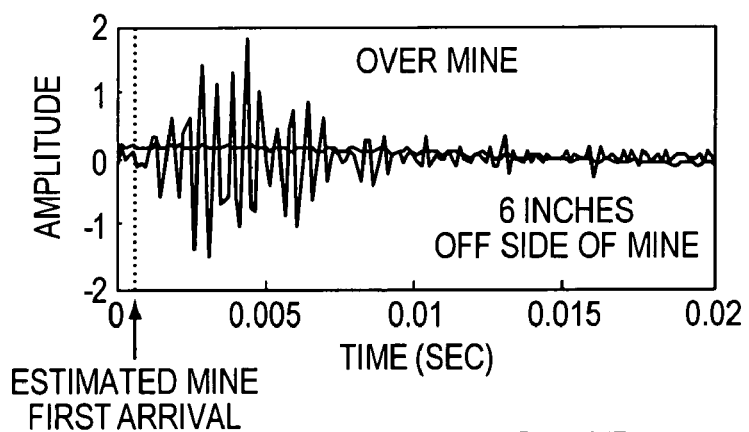
FIG. 1B shows the measurement response of a laser vibrometer to detection of a landmine.

FIG. 1B illustrates the measurement response of a conventional laser vibrometer when buried VS50 anti-personnel mines are exposed to to sound produced by PAA 110. As shown in the response curves, very little response (the substantially flat line) is observed for the off-mine position, but the strongly oscillating vibrometer output readily reveals the over-mine position.

Landmine Detection

When acoustic waves come in contact with the ground, most of the energy reflects back into the air. A small percentage of these waves, however, couples to the ground, causing ground motion that transmits a series of seismic waves. These seismic waves consist of a surface wave (the Rayleigh wave) that travels at the air/soil interface, and body waves that travel in the soil (a shear wave and two compressional waves). The Rayleigh wave, the shear wave, and one of the compressional waves, called the fast P-wave, propagate within the solid granular matrix in soil at speeds typically greater than several hundred meters per second. At these speeds, and over much of the audible bandwidth, the associated seismic wavelengths are considerably larger than landmine dimensions. The second compressional wave, called the slow P-wave, exhibits speeds slower than the other seismic waves and is controlled by the void space in soil (which determines porosity and permeability) and the fluid content (both air and water) in soil pores. Some slow P-waves are observed to travel significantly more slowly than the speed of sound in air, thus producing wavelengths at the scale of the size of land mines.

It appears that 100 to 300 Hz is a critical frequency band that can excite primary resonances in anti-tank mines. An acoustic frequency band from 200 to 600 Hz is typically used to excite the primary resonances in anti-personnel mines. We have observed additional resonances at frequencies above 1 kHz, but higher-frequency resonance magnitudes are significantly smaller than those of the primary resonances. It may be difficult to generate sufficient acoustic power at 100 Hz at safe standoff ranges. However, PAA 110 is likely to deliver the needed power at frequencies above 200 Hz, which is useful in exciting resonances in anti-personnel mines and some anti-tank mines. Pulse-compression methods can be used to exploit higher-frequency backscatter returns for detection of both antitank and anti-personnel mines.

PAA 110 has the ability to produce relatively higher power sound levels at frequencies above primary mine resonances. Despite the drop in higher-frequency mine resonance magnitudes, a large backscattered return off the mine is possible. The percentage of backscattered return is expected to increase as the acoustic and seismic wavelengths become smaller and approach the size of the mine. In addition, experimental results show that the backscattered return may not depend on viewing angle as strongly as the resonant returns, and thus may permit forward viewing with a laser vibrometer appropriate for standoff detection. At higher frequencies, slow seismic interface waves can be generated between the soil and mine. These waves can scatter and interfere with mines in their path and produce horizontal and vertical motion components at the ground surface. In some cases, strong horizontal motion can dominate the interface wave particle orbit.

Detection of Flaws in Sheathed Concrete Structures

The present invention can be used to locate flaws and damage in concrete structures wrapped with, for example, fiberglass or polymer sheathing. Such structures include bridge piers, concrete columns, load-bearing concrete members, etc. We have observed that airborne acoustic waves couple to rigid structures and generate a vibration field over the surface of a structure. Local heterogeneities in the structure can cause local vibration anomalies that are a function of the heterogeneity dimensions and mechanical properties. These vibration anomalies can be measured using laser vibrometer 115 (or other vibration-measurement system) directed at the target surface, and the resulting measurements, in turn, can be used to remotely detect, map, and quantify or infer aspects of the target's heterogeneities.

Figure 2:
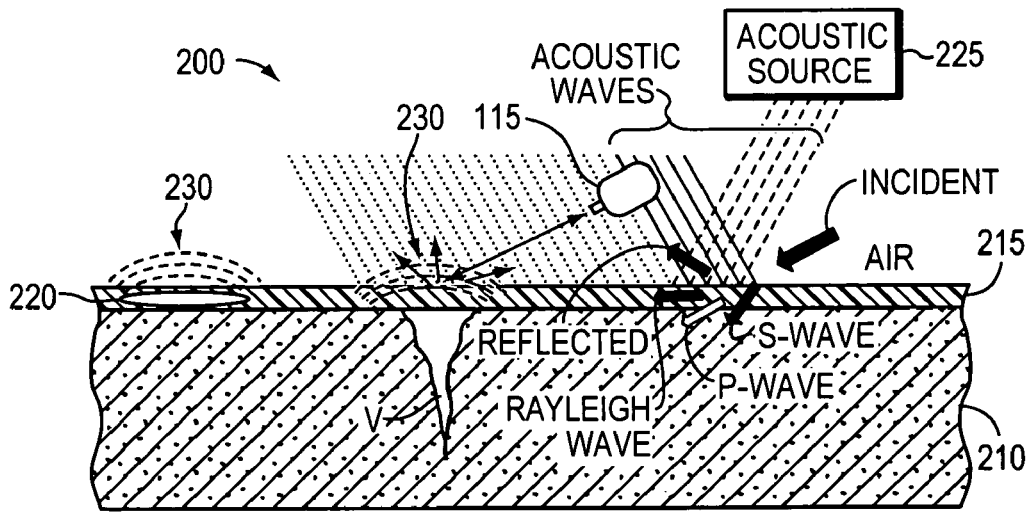
FIG. 2 schematically illustrates detection of voids or defects in sheathed concrete structures in accordance with the invention.

With reference to FIG. 2, a structure 200 includes a concrete member 210 covered by a composite fiber-reinforced plastic (CFRP) sheath 215 has a void V that is covered by sheath 215 and is therefore undetectable by visual inspection. There is also a region 220 of delamination, i.e., de-anchoring of sheath 215 from the surface of member 210. An acoustic source 225 transmits an acoustic signal to excite vibrations in the sheath 215 over the concrete member 210. Laser vibrometer 115 or another suitable vibration-measurement system is then used to measure the vibration field over the surface of sheath 215. Acoustic source 225 can be a PAA (as described above), which transmits a highly directional acoustic beam, or may instead be a conventional loudspeaker that transmits an omni-directional sound beam.

When acoustic waves come in contact with solids, most of the energy reflects back into the air. A small percentage of these waves, however, couples to the solid, causing motion that transmits a series of seismic waves. These seismic waves consist of a surface wave (the Rayleigh wave) that travels at the air/solid interface, and body waves that travel in the solid (shear and compressional waves). The Rayleigh wave travels along the boundary of the and air. At a specific frequency, the Rayleigh wave will produce resonances 230 in sheath 215 that are a function of the void, crack or delamination dimension. The Rayleigh wave over a finite-length void can be described in terms of two harmonic waves traveling in opposite directions:

$$y(x,t) = A e^{j(\omega t - kx)} + B e^{j(\omega t + kx)} \quad \text{(Eq. 1)}$$

where y is the vibration amplitude as a function of distance along the void in x and time, t. A and B are complex amplitudes that are determined by the boundary conditions. The quantity k is the wave number and ω is the angular frequency. A standing wave will form through the length L of the void. The wave, of wavelength λ, forms nodes and antinodes at half wavelengths and forms resonances at n frequency harmonics:

$$f_m = \frac{2n-1}{4} \frac{c}{L} \quad \text{(Eq. 2)}$$

where c is the acoustic wave speed and L is the length of the void or extent of the delamination.

This approach facilitates detection and imaging of flaws such as voids, major fractures, and unbonded areas beneath sheathing 215. A loudspeaker or PAA-based system can operate at ranges exceeding 10 meters or at closer ranges without direct contact to the structure. When using a laser, the laser vibrometer beam spot size may be on the order of a millimeter and allows spatial sampling over the sample at the same order.

Figure 3A:
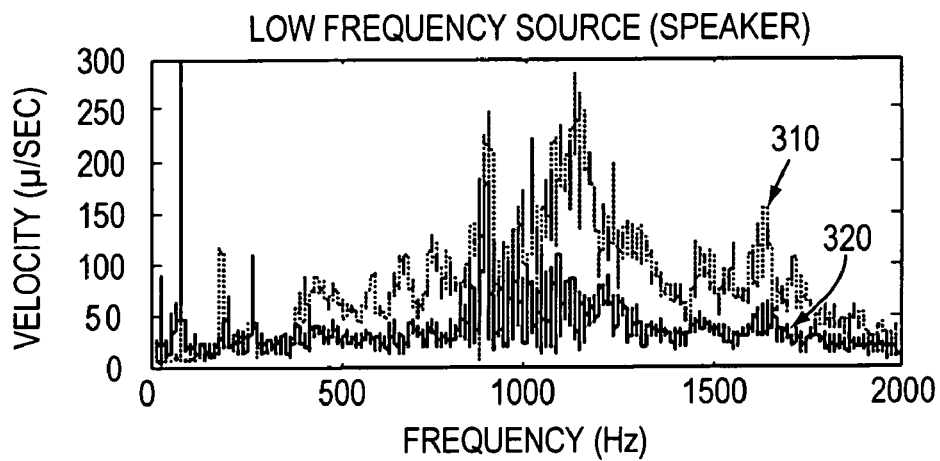
FIG. 3A illustrates the signature associated with a void in a concrete structure, excited at a low frequency.
Figure 3B:
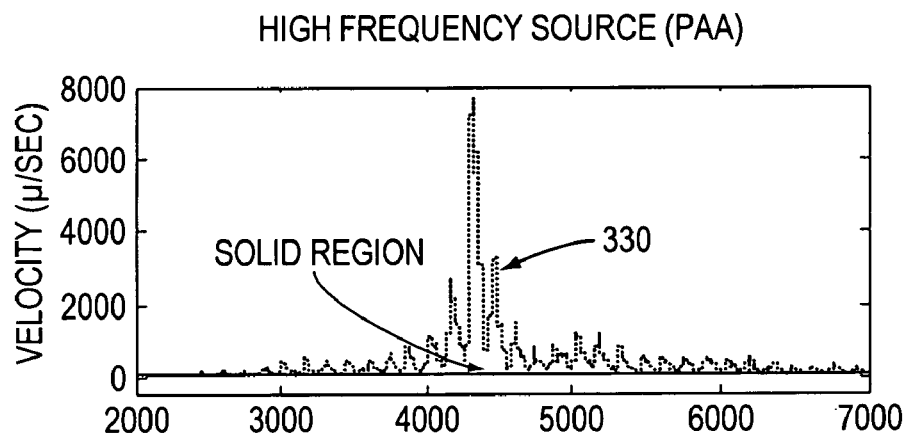
FIG. 3B illustrates the signature associated with a void in a concrete structure, excited at a high frequency.
Figure 3C:
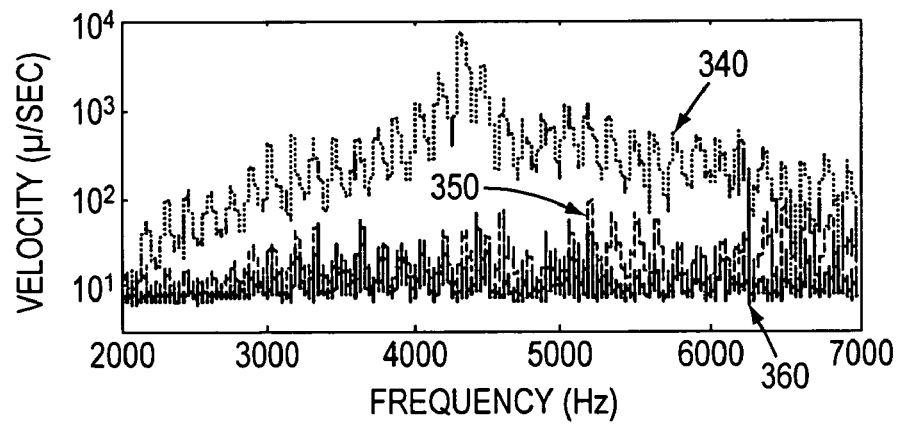
FIG. 3C illustrates signatures associated with large and small voids in a concrete structure, excited at a high frequency.

FIGS. 3A-3C illustrate vibration signatures obtained for a solid cement cylinder containing a single 1.5 square inch void in its surface. The entire sample is wrapped in fiberglass sheathing covering the void. The plots show the vibration velocities measured at single locations: one directly over the void and one over a solid cement region as a function of acoustic excitation frequency. FIG. 3A depicts results for a loudspeaker source, which drives a linear chirp from 50-2000 Hz. The signature 310 over the void exhibits a larger velocity amplitude than the signature 320 over the intact region and may be useful for detecting an anomalous region in the sample. FIG. 3B shows the response 330 of the void excited by a higher acoustic frequency band (2000-7000 Hz) using PAA 110. In this case, the void exhibits a large resonance velocity at 4300 Hz. The velocity amplitude at the peak resonance is over 30 dB greater than the return from an intact region.

As shown in FIG. 3C, the size of void can be inferred from the peak resonance frequency. A large void elicits a strong signature 340. Using a sound speed of 340 m/s, the ½ wavelength of the resonance is 1.5 inches, precisely the width of the void. A smaller (e.g., 3-10 times smaller) void produces a weaker signature 350, while the signature 360 over the intact region exhibits the smallest velocity amplitude. Accordingly, controller 120 can, based on Eq. 2, scan incoming signals for voids of specific dimensions or a dimensional range (e.g., in order to filter out voids below a certain size), or can estimate the sizes of voids as they are detected.

Although the present invention has been described with reference to specific details, it is not intended that such details should be regarded as limitations upon the scope of the invention, except as and to the extent that they are included in the accompanying claims.

What is claimed is:

1. A method of remotely localizing an object or defect beneath a surface, the method comprising the steps of:
   a. generating a directive ultrasonic acoustic beam with an acoustic source located more than 10 meters from the surface, the ultrasonic acoustic beam including a modulated, inaudible high-frequency signal and an audible low-frequency signal;
   b. directing the acoustic beam through air at the surface, the air causing demodulation of the acoustic beam and entry of the low-frequency signal into the surface at a sound pressure level of greater than 100 dB; and
   c. detecting vibrations at the surface characteristic of the object or defect to thereby localize the object or defect.

2. The method of claim 1 wherein the object or defect is a landmine and the surface is the ground.

3. The method of claim 1 wherein the object or defect is a void and the surface comprises a sheath enveloping a concrete structure.

4. A system for remotely localizing an object or defect beneath a surface, the system comprising:
   a. an acoustic source located more than 10 meters from the surface for generating and directing towards the surface a directive ultrasonic acoustic beam including (i) a modulated, inaudible high-frequency signal and (ii) an audible low-frequency signal that reaches a sound pressure level of greater than 100 dB at the surface;
   b. a vibration detector for detecting, without physical contact, vibrations at the surface caused by the acoustic beam; and
   c. an analysis module for localizing the object or defect based on the detected vibrations.

5. The system of claim 4 wherein the acoustic source comprises a parametric acoustic array.

6. The system of claim 4 wherein the acoustic source comprises at least one loudspeaker.

7. The system of claim 4 wherein the detector is a laser vibrometer.

8. The system of claim 4 further comprising means for steering the acoustic source.

9. The system of claim 4 wherein the analysis module is configured to characterize objects or defects based on a match between the detected vibrations and a stored signature.

10. The system of claim 4 wherein the analysis module is configured to characterize objects or defects analytically.

11. The system of claim 4 wherein the analysis module is configured to characterize objects or defects based on thresholding.

12. The system of claim 4 wherein the analysis module is configured to estimate a dimension associated with an object or defect.

* * * * *